United States Patent [19]

Knight et al.

[11] Patent Number: 4,649,911
[45] Date of Patent: Mar. 17, 1987

[54] SMALL PARTICLE AEROSOL GENERATOR FOR TREATMENT OF RESPIRATORY DISEASE INCLUDING THE LUNGS

[75] Inventors: Jack V. Knight; Samuel Z. Wilson, Jr., both of Houston, Tex.

[73] Assignee: Baylor College of Medicine, Houston, Tex.

[21] Appl. No.: 837,463

[22] Filed: Mar. 7, 1986

Related U.S. Application Data

[63] Continuation of Ser. No. 530,290, Sep. 8, 1983, abandoned, which is a continuation-in-part of Ser. No. 304,149, Sep. 21, 1981, abandoned.

[51] Int. Cl.$^4$ ............................................. A61M 11/00
[52] U.S. Cl. ........................... 128/200.21; 128/203.15; 239/338
[58] Field of Search ...................... 128/200.14, 200.21, 128/203.12, 203.15; 239/338

[56] References Cited

U.S. PATENT DOCUMENTS

| | | | |
|---|---|---|---|
| 3,379,194 | 4/1968 | Ziermann | 128/200.21 |
| 3,395,703 | 8/1968 | Chouinard et al. | 128/200.21 |
| 3,580,249 | 5/1971 | Takaoka | 239/338 X |
| 3,603,308 | 9/1971 | Spradling et al. | 128/200.21 |

OTHER PUBLICATIONS

Young et al., "Continuous Aerosol . . . Nebulizer", J. Clin. Micro., Feb. 1977, pp. 131–136.
Stephen et al., "Treatment of Influenza . . . " Anti. Agents Chemo., Aug. 1975, pp. 154–158, vol. 8, No. 2.
Berendt et al., "Response of Influenza . . . " Anti. Agents Chemo., vol. 11, No. 6, Jun. 1977, pp. 1069–1070.
Walker, et al., "Small Particle Aerosols . . . ", J. Infect. Diseases, vol. 133, Supp., Jun. 1976, pp. A140–144.
Stephen et al., "Therapeutic Effects . . . Mice", Anti. Agents Chemo., Sep. 1976, pp. 549–554, vol. 10, No. 3.
Arensman et al., "Effects of Small Particles . . . ", Anti. Agents Chem., vol. 12, No. 1, pp. 40–46, Jul. 1977.
Knight et al., "Small Particle Aerosols . . . " Ribavirin: A . . . Agents, pp. 129–145, 1980.
Wilson et al., "Amantadine Small Particle Aerosol . . . ", Proc. Sol. Exper. Biol. Med. 1979, 161: 350–354.
Wilson et al., "Amantadine and Ribavirin . . . ", Anti. Agents Chemo. 1980, 17(4): 642–648.
Knight et al., "Amantadine Aerosol in Humans", Anti. Agents Chemo. 1979, 16(4): 572–578.

Primary Examiner—Lee S. Cohen
Attorney, Agent, or Firm—Fulbright & Jaworski

[57] ABSTRACT

Disclosed is a small particle aerosol or nebulizer apparatus effective for providing small particles of aerosol containing drug; that is, particles having a maximum diameter of 10 microns but predominantly 1–2 microns, effective for treating the respiratory tract and lungs and providing respiratory retention of most drugs of at least 50 milligrams up to about 100 milligrams per hour. It has features which result in more efficient output of aerosol containing drugs, provides very small aerosol particles which are readily deposited in the lower respiratory tract and lungs, and provides even flow of drug containing aerosol to a patient when exhaling and inhaling.

7 Claims, 7 Drawings Figures

Fig. 3

SMALL PARTICLE AEROSOL GENERATOR FOR TREATMENT OF RESPIRATORY DISEASE INCLUDING THE LUNGS

REFERENCE TO RELATED APPLICATION

The present application is a continuation of application Ser. No. 530,290, filed Sept. 8, 1983, abandoned which in turn is a continuation-in-part of application Ser. No. 304,149, filed Sept. 21, 1981, abandoned.

BACKGROUND OF THE INVENTION

1. Field of the Invention

The present invention relates to apparatus for small particle treatment of the respiratory tract including the lungs.

2. Prior Art

As a result of suggestions made by one of the inventors, in consultations at Ft. Detrick, Md., scientists at the U.S. Army Medical Research Institute of Infectious Diseases in 1975 adapted a Collison nebulizer to deliver a continuous flow of small particle aerosols to mice infected with influenza virus. This system was described by Young and his associates in 1977 (Young, H. W., Dominik, J. W., Walker, J. S., Larson, E. W. Continuous aerosol therapy system using a modified Collison nebulizer. J Clin Microb 1977; 5(2):131-136). Several papers were published subsequently dealing with the use of this technology to treat influenza infections in mice with rimantadine (Stephen, E. L., Dominik, J. W., Moe, J. B., Spertzel, R. O., Walker, J. S. Treatment of influenza infection of mice by using rimantadine hydrochloride by the aerosol and intraperitoneal routes. Antimicrob Ag Chemother 1975; 8(2):154-158, amantadine and ribavirin Walker, J. S., Stephen, E. L., Spertzel, R. O. Small particle aerosols of antiviral compounds in treatment of type A influenza pneumonia in mice. J Infect Dis 1976; 133:A140-A144). Another study compared the effect of ribavirin given by the intraperitoneal and aerosol routes in influenza infections in mice (Stephen, E. L., Dominik, J. W., Moe, J. B., Walker, J. S. Therapeutic effects of ribavirin given by the intraperitoneal or aerosol route against influenza virus infections in mice. Antimicrob Ag Chemother 1976; 10(3):549-554) and on the physiological alterations in mice with influenza, untreated and treated with ribavirin aerosol (Arensman, J. B., Dominik, J. W., Hilmas, D. E. Effects of small particle aerosols of rimantadine and ribavirin on arterial blood pH and gas tensions and lung water content of A2 influenza-infected mice. Antimicrob Ag Chemother 1977; 12(1):40-46). Berendt and associates made further studies of treatment of influenza in mice with ribavirin aerosol (Berendt, R. F., Walker, J. S., Dominik, J. W., Stephen, E. L. Response of influenza virus-infected mice to selected doses of ribavirin administered intraperitoneally or by aerosol. Antimicrob Ag Chemother 1977; 11(6):1069-1070).

Based on the foregoing work, technology was adapted for human use by the inventor in his laboratory (Wilson, S. Z., Knight, V., Moore, R., and Larson, E. W. Amantadine small particle aerosol: generation and delivery to man. Proc Sol Exper Biol Med 1979; 161:350-354). Studies in mice in the inventor's laboratory confirmed the earlier results and, in addition, showed that a substantial therapeutic effect was demonstrable when treatment was delayed for as long as five days after inoculation (Knight, V., Wilson, S. Z., Wyde, P. R., Drake, S., Couch, R. B., Galegov, G. A., Novokhatsky, A. S. Small particle aerosols of amantadine and ribavirin in the treatment of influenza. In Ribavirin: A Broad Spectrum Antiviral Agent. Smith, R. A. and Kirkpatrick, W. (ed), Academic Press, Inc., New York 1980; pp. 129-145; Wilson, S. Z., Knight, V., Wyde, P. R., Drake, S., Couch, R. B. Amantadine and ribavirin aerosol treatment of influenza A and B infection in mice. Antimicrob Ag Chemother 1980; 17(4):642-648; Knight, V., Bloom, K., Wilson, S. Z., Wilson, R. K. Amantadine aerosol in humans. Antimicrob Ag Chemother 1979; 16(4):572-578). These studies additionally show that a combination of ribavirin and amantadine increase the effectiveness of therapy.

While the animal studies, in this case mice, demonstrated the efficacy of aerosol treatment, and encouraged human trial, the human trials were done with the realization that therapeutic effect, tolerance and toxicity may be quite different in man and animals. For example, in Wilson, et al, 1979, Amantadine Small Particle Aerosol: Generation and Delivery to Man, supra, in using the arbitrary criteria for retention of aerosol in mice and man, the estimated dosages in mice were approximate four-fold those in man when similar exposure periods were employed. Up until the present development, there was no determination made of the aerosol concentration of the drug which provided an effective, tolerant and nontoxic concentration for man. In addition, most available nebulizers provide coarse particles, that is particles having a mean diameter of 10 microns and over which are too coarse to penetrate effectively into the lungs.

While the small particle or nebulizer apparatus described and used in Wilson, et al, 1979, generated small particles and produced the results there set forth, it had the following disadvantages, (1) the valve from the bag to the mask would clog with precipitated drugs from the aerosol and the mere insertion of mechanical valves, however efficient, inevitably creates some obstruction that in some degree obstructs the flow of aerosol to the patient; (2) the air exhaled by the patient is forced into the aerosol stream flowing to the patient and the patient then inhales his own exhaled air from which the drug had been removed; and (3) the efficiency of the apparatus needed to be improved to provide a higher concentration of drug per liter of aerosol.

U.S. Pat. No. 4,211,711 is directed to ribavirin, and the small particle aerosol or nebulizer apparatus of this invention is particularly well suited to deliver small particle ribavirin for treatment of the respiratory tract including the lungs.

The most pertinent prior art relating to the present invention known to the applicant is the prior art set forth above in this section of the Background of the Invention.

SUMMARY OF THE INVENTION

The present invention is directed to improved apparatus which overcomes the above disadvantages and which provides continuous flow of small particle aerosol for treatment of diseases of the respiratory tract and the lung of man in which the drug is in concentrations which are effective and at the same time which man can tolerate, which are nontoxic for man and in which the drug is effectively deposited in the lungs. The aerosol or nebulizer apparatus of the present invention provides small particle aerosol to the patient with a maximum diameter of 10 microns with predominately particles having a mean diameter in the range of 1 to 2 microns. Advantageously, aerosol or nebulizer apparatus of the present invention has no valves or other obstructions to the free flow of aerosol to the patient, has an exhaust and reservoir tube which permits even flow of aerosol to the patient while inhaling and exhaling, has a dryer which dries the aerosol thereby reducing its particle size thus permitting the aerosol to readily penetrate into the lungs, the aerosol being hydrated by moisture in the respiratory tract and the lungs, and which provides substantially improved concentrations of drug per liter of aerosol. Advantageously, this improved aerosol or nebulizer apparatus provides aerosol concentrations of drugs, such as ribavirin with a respiratory retention of about 50 mg. per hour in the adult and similar retention efficiency corrected for weight in infants and children, but which can be increased to a maximum of about 100 mg. per hour resulting in particularly good results in the treatment of influenza. Amounts below such minimum respiratory retention can be used for potent drugs effective in low doses. Higher concentrations risk pulmonary reactions. The provision of aerosol concentrations of the drug sufficient for respiratory retention of 50 mg. per hour to about 100 mg. per hour provides a therapeutic effect and safety in man; although lower doses of powerful drugs, such as chemotherapy and antiallergic drugs could be used.

The small particle aerosol or nebulizer apparatus is particularly effective in providing doses of drug lower than usually required by oral or parenteral administration, thus reducing the risk of toxicity of larger doses but with the advantage of immediate deposition on the infected pulmonary surface. Particularly good results have been obtained in the treatment of influenza.

Accordingly, it is an object of the present invention to provide an improved small particle aerosol generator or nebulizer effective for treatment of respiratory diseases with small particle aerosol concentrations of drugs which are therapeutically effective and safe in man.

It is a further object of the present invention to provide such an improved small particle aerosol generator or nebulizer by which diseases of the lung and respiratory tract in humans are treated by a continuous flows of small particle aerosol concentration of drugs sufficient for respiratory retention in man of from about 50 mg. per hour to about 100 mg. per hour.

It is a further object of the present invention to provide an improved aerosol generator or nebulizer which produces a steady stream of small particles, that is, particles having a maximum diameter of 10 microns and predominately in the range of 1 to 2 microns by which drug aerosol concentrations for the treatment of diseases of the respiratory tract and lungs can be given safely and effectively.

A further object of the present invention is the provision of a small particle aerosol generator or nebulizer useful in the treatment of influenza virus infection in humans by inhalation of ribavirin, amantadine, or rimantadine, or mixtures thereof in small particle aerosol form in amounts or concentrations to be effective for treating influenza which the human can tolerate and which are safe to humans. By such improved small particle aerosol generator or nebulizer, ribavirin may also be provided to the patient in treatment of respiratory syncytial virus infections, parainfluenza virus infections, and other respiratory virus infections that are sensitive to the drug in vitro.

A further object of this invention is the provision of such a small particle aerosol generator or nebulizer which has no obstructions, such as valves, to a free flow of aerosol to the patient thereby avoiding clogging of the generator or nebulizer with precipitated aerosol.

A further object of the present invention is the provision of a small particle generator or nebulizer which provides an even flow of aerosol to the patient while the patient is inhaling and exhaling.

A further object of the present invention is the provision of a small particle generator or nebulizer in which the aerosol contains high concentrations of drugs.

Other and further objects, features and advantages appear throughout this specification and claims.

BRIEF DESCRIPTION OF THE DRAWING

FIG. 7 is a partial view illustrating a simplified small particle aerosol generator or nebulizer apparatus in which the reservoir is in the nebulizer flask.

DESCRIPTION OF PREFERRED EMBODIMENTS

Figures 1, 2:
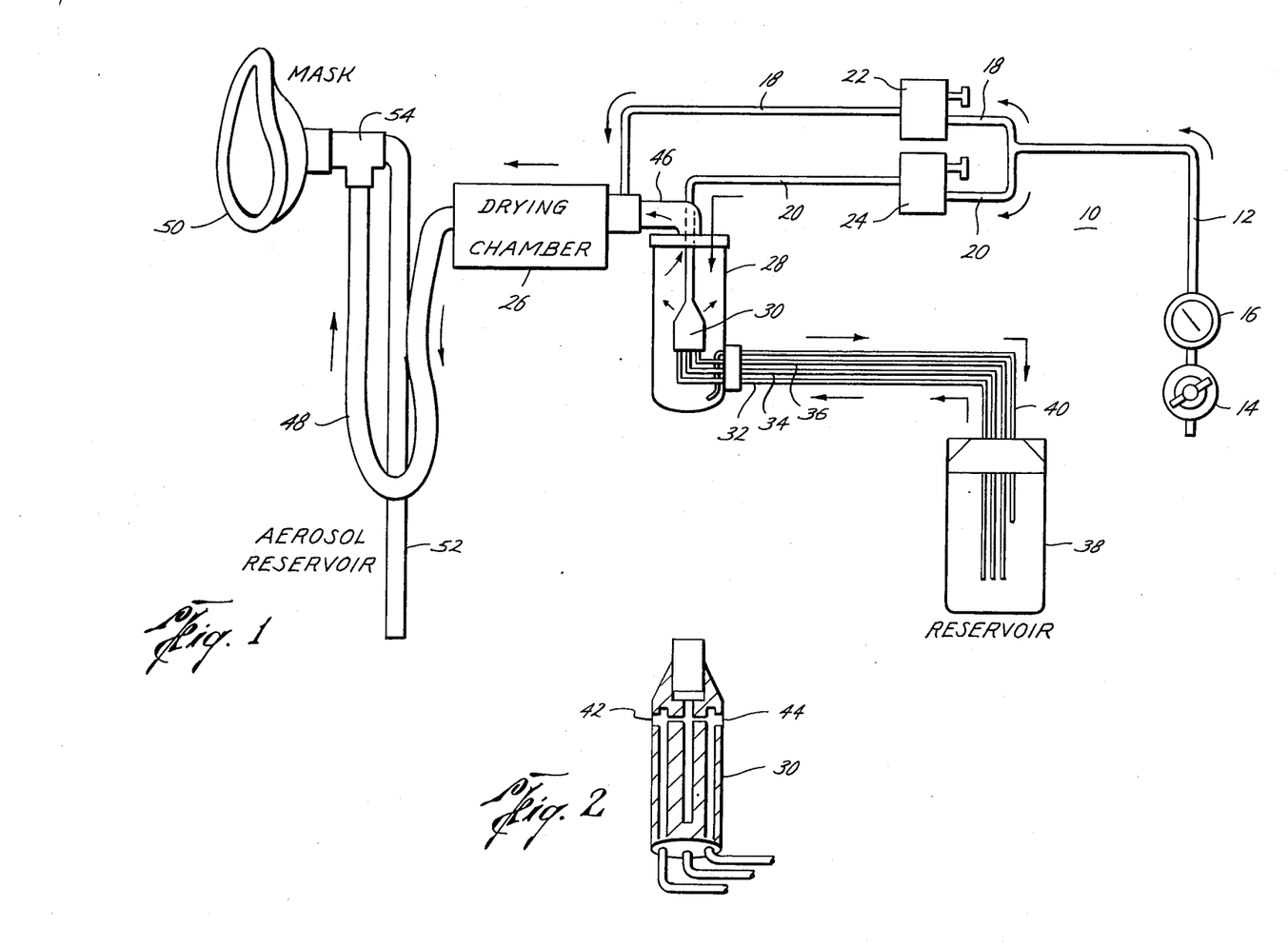
FIG. 1 is a flow diagram illustrating a small particle aerosol generator or nebulizer of the invention.
FIG. 2 is an enlarged elevational view of the nebulizer head of FIG. 1.

Referring now to the drawings and particularly to FIG. 1, a small particle aerosol or aerosol nebulizer apparatus of the present invention is illustrated and designated by the referenced numeral 10, which includes an inlet tube 12 having the pressure regulator 14 and pressure gauge 16 connected to a portable air compressor, a wall air outlet from a central service compressor, or to air from a compressed air cylinder, not shown. Dried air enters the inlet tube 12 after being regulated by the pressure regulator 14 to a desired pressure of 26 psi. The inlet tube 12 is connected to the tubes 18 and 20, which each contains a flow meter 22 and 24, respectively, which regulates the flow of air in the lines 18 and 20, here shown as 2-3 liters per minute in the line 18 and 9-10 liters per minute in the line 20. The line 18 contains preferably dry dilution air which passes into the drying chamber 26 and the line 20 is connected to the nebulizer chamber 28 having the nebulizer head 30 in it. The humidity of the aerosol particles is reduced in the drying chamber 26 preferably by mixing with dry dilution air; although, any form of dryer can be used to reduce the humidity of the aerosol particles and hence their size.

The nebulizer head 30 has the feed lines 32, 34 and 36 extending into the drug reservoir 38, here shown as containing 400 cc. of the drug in desired concentrations for treatment of the patient. A return line 40 is provided from the nebulizer chamber 28 to the drug reservoir 38. The nebulizer head 30 (FIG. 2) is provided with the atomizer ports 42, a port not visible and 44 which are in fluid communication with the feed lines 32, 34 and 36. The flow of air into the nebulizer head 30 in line 20 aspirates or sucks the drug solution from the reservoir in the lines 32, 34 and 36, the atomizer port in communication with line 34 not being shown in this view.

Referring now to FIG. 1 the atomized drug derived from the solution then flows through the passage 46 into the drying chamber 26; effluent drug liquid is recirculated to the fluid reservoir 38 in the return line of 40.

The dry dilution air reduces the humidity of the aerosol particles in the drying chamber 26; the dried and shrunken particles then pass through the flexible tubing 48 to the face mask 50 for the patient, not shown. The dried and shrunken particles are small enough to pass through the respiratory tract into the lungs, the moisture in the respiratory tract and lungs rehydrating the dried aerosol drug particles for effective treatment. In addition no valve or other obstruction is provided in the aerosol flow tubing 48 to the face mask which cause precipitation of drug from the aerosol causing clogging, decreased aerosol flow and the like.

A flexible line 52 is provided in the connection 54 to the mask 50 which provides for even flow of drug-containing aerosol to the patient. The flexible line or tube 52 functions to receive and contain air exhaled by the patient which would otherwise be forced into the aerosol inflow tube 48 retarding the inflow of drug-containing aerosol to the patient. When that occurs, such as when the line or tube 52 is omitted, the patient inhales the air just exhaled from which the drug had been removed. The continuous flow of fresh aerosol flushes the line or tube 52 of exhaled air and the tube acts as a reservoir to supply aerosol to the patient during peak inspiration.

Satisfactory results have been obtained by regulating the air pressure to 26 psi, and having a flow rate of dilution air of 2–3 liters per minute with air passing into the nebulizing chamber 28 of about 9–10 liters per minute which results in a flow of about 11–13 liters per minute to the face mask 50. Other pressures and flow rates can be utilized; however, highly satisfactory results have been obtained at this pressure and these flow rates using this particular nebulizer.

It should be noted that most available nebulizers deliver only a coarse mist, 10 microns diameter and over, which deposit drugs in the nose and throat areas and not in the lungs. The particle size in a coarse mist and a small particle aerosol is quite different. The particle size in a coarse mist is usually greater than 20 microns in diameter, whereas the aerodynamic mass median diameter (A.M.M.D.) of the small particles in the present invention is about 1.3 microns with 95% less than 5 microns, although the diameter of the particles can be as high as 10 microns provided they are predominately up to 2 microns in diameter.

Figure 3:
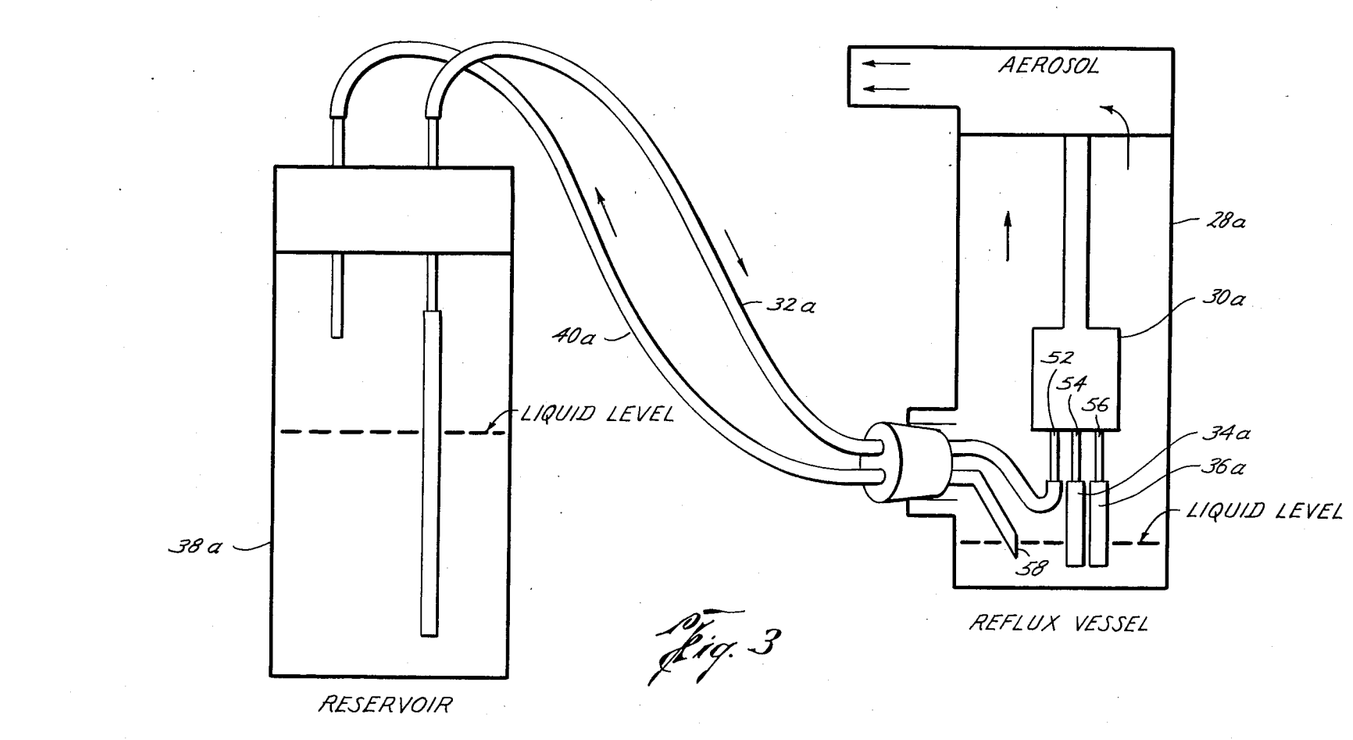
FIG. 3 illustrates a more efficient arrangement of the flow of drug containing liquid between the reservoir and the reflux vessel which provides optimum results with less potential for malfunction.

An alternative arrangement to supply drug solution to the aerosol nebulizers and to return unaerosolized solution to the reservoir is show in FIG. 3, in which the letter "a" is added to numerals corresponding to the nebulizer shown in FIG. 1 for convenience of reference. Liquid is drawn from the reservoir 38a through silicone tubing (Masterflex, 0.063 inches, internal diameter) through steel tubing in the cap of the reservoir, thence through silicone tubing 32a to a stopper in an opening leading to the reflux vessel 28a. From the stopper the fluid flows through the continuation of silicone tube 32a to one of the three nebulizer ports 52 where it provides drug solution to be aerosolized. The remaining two nebulizer ports 54 and 56 are supplied from silicone tubing (Masterflex, 0.031 inches, internal diameter) whose tips are submerged in the fluid in the reflux vessel. Fluid that is not aerosolized is collected in the bottom of the reflux vessel and returned to the reservoir via the stainless steel pickup tube 40a with a vertical bevel 58 and silicone tubing. The vertical bevel allows air to return with liquid to the reservoir in small bubbles. Large bubbles enter the system when the tip is not so bevelled and may lead to obstruction in the silicone tubing. The aerosol generator operates otherwise as described in connection with FIGS. 1 and 2.

Figure 4:
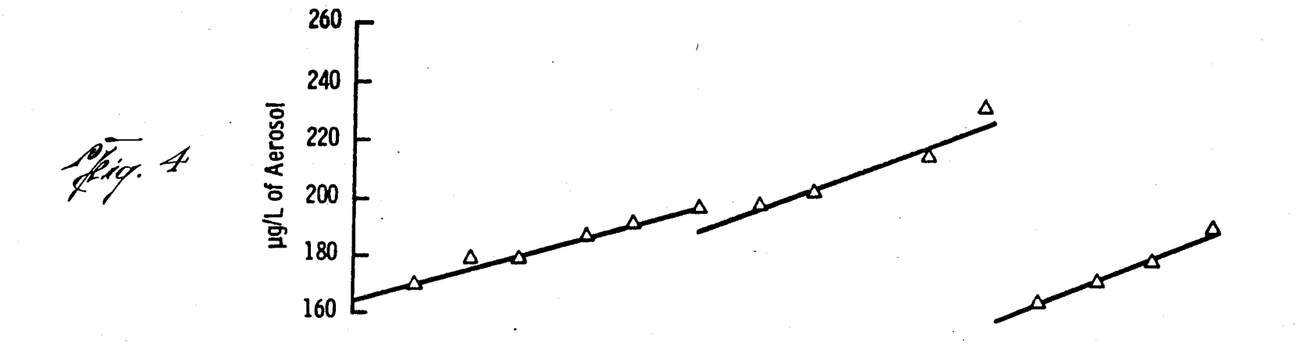
FIG. 4 is a graph in which concentration of ribavirin in aerosol is plotted against time.
Figure 5:
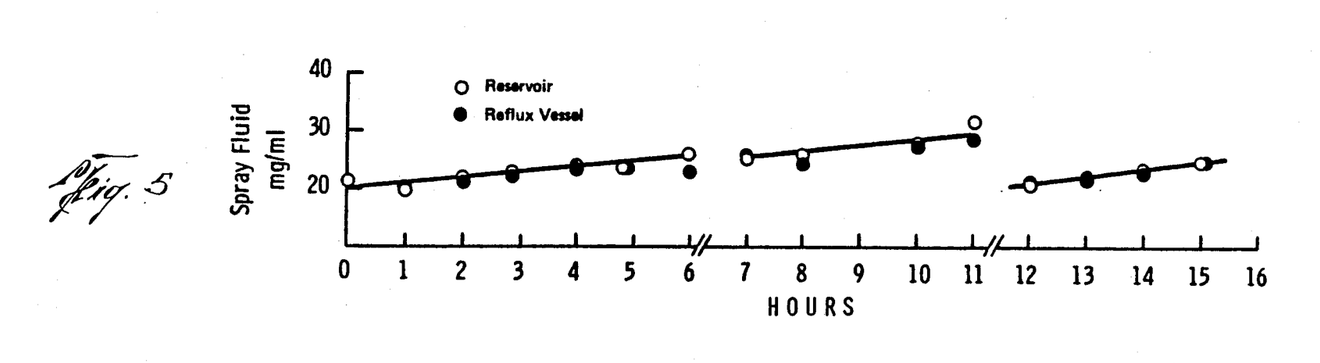
FIG. 5 is a graph in which volume of drug in the spray fluid from the reservoir and reflux vessel are plotted against time.
Figure 6:
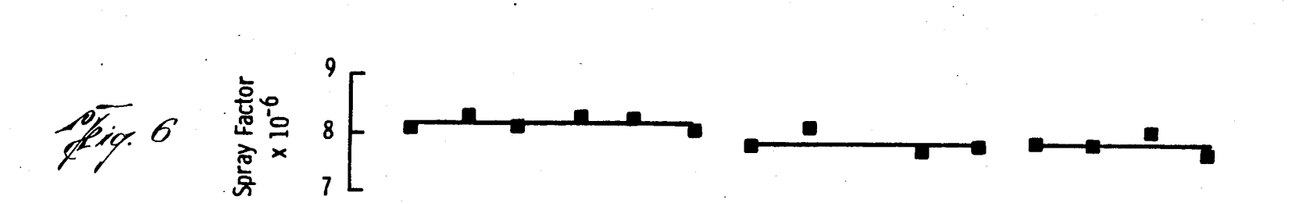
FIG. 6 is a graph of the spray factor (calculated).

Characteristics of ribavirin aerosol produced by the arrangement in FIG. 3 are shown in FIGS. 4, 5 and 6. With 20 mg. per ml. of ribavirin in the aerosol reservoir 38a the concentration of ribavirin in the aerosol was 160 micrograms per liter at initiation of generation, as shown in FIG. 4. After 6 hours operation the concentration of ribavirin in the aerosol was 200 mg/l, indicative of the expected excess of evaporation of water during operation of the generator. The concentration of ribavirin in the spray fluid, FIG. 5 and in the aerosol, FIG. 4 increased proportionately to maintain a uniform spray factor (concentration in aerosol in micrograms per liter divided by concentration in spray fluid in micrograms per liter) of about $8 \times 10^{-6}$, as calculated and shown in FIG. 6. Further measurements were made after overnight delays between 6 and 7 hours and 11 and 12 hours. Differences in concentration at these times were due to intentional dilution of reservoir solution with distilled water. The data indicate highly efficient aerosol generation. The particle size, aerodynamic mass median diameter, at the fourth hour of aerosol generation was 1.35 microns, representative of values obtained in measurements at different times with various methods of operation.

Referring now to FIG. 7, where the reference letter "b" has been added to numerals corresponding to numerals of FIGS. 1 and 2 and FIG. 3, the aerosol or nebulizer apparatus has been simplified by removal of the reservoir 38 (FIG. 1), and 38a (FIG. 3) and by making the nebulizer chamber 28b large enough to contain the drug solution for continuous aerosol use, the chamber 28b serving as a common reflux and reservoir chamber. The nebulizer chamber 28b is designed to hold 300 ml of solution which is sufficient for 12 or more hours of operation. Fluid is drawn to the three nebulizer ports through silicone masterflex tubing, 0.031 inches inside diameter. The ends of the tubes 32b, 34b and 36b project nearly to the bottom of the chamber 28b. In other respects this embodiment is identical to the aerosol or nebulizer apparatus of FIGS. 1 and 2 and FIG. 3.

During a period of 5 hours of operation of the aerosol apparatus or nebulizer of FIG. 7, the initial concentration of ribavirin in the nebulizer flask (300 ml volume) increased from 31 mg per ml to 35.4 mg per ml (about 15 percent) a degree of concentration similar to that observed with the apparatus described in FIG. 3. The output of drug in small particle aerosol increased from 325 micrograms per liter initially to 343 micrograms per liter at 5 hours, an increase in concentration of 5.5 percent, a value similar to results with the apparatus described in FIG. 6. The dosage used in this study was about 50 percent larger than used in previous clinical studies.

Unexpectedly, the efficiency of the operation of the modified aerosol or nebulizer apparatus of FIG. 7 is greater than that obtained with the apparatus described in FIG. 3. This is measured by the spray factor, an index of the output which is the concentration of drug in the aerosol in micrograms per liter divided by the concentration of the drug in the liquid solution in micrograms per liter. The spray factor for the apparatus in FIG. 3 was $8 \times 10^{-6}$ while it was $1.1 \times 10^{-5}$ for the apparatus in FIG. 7 (37.5 percent higher aerosol output from apparatus in FIG. 7 as compared to that in FIG. 3).

The following Table 1 illustrates the improvement in efficiency of the nebulizers of FIGS. 1 (and 2), 3 and 7.

TABLE 1

| FIG. | Reservoir Drug Concentration | Aerosol Concentration |
| --- | --- | --- |
| 1 & 2 | 15 mg/ml | 64 μg/liter |
| 3 | 15 mg/ml | 120 μg/liter |
| 7 | 15 mg/ml | 165 μg/liter |

The nebulizer of FIG. 7 is presently preferred due to its unexpected high efficiency. The nebulizer of FIG. 3 provides substantially improved results over that of FIGS. 1 and 2, which while not nearly as efficient as those of FIG. 7 provides satisfactory results.

The following examples are illustrative of the effectiveness of the treatment of lung disease with small particle drug aerosols having a respiratory retention of from about 50 mg. per hour to about 100 mg. per hour.

EXAMPLE 1

College students with illness suggestive of influenza of less than 24 hours duration were invited to participate in the study and were admitted to the Student Health Center. They were randomly divided into treatment or control groups. Sixteen of 22 patients assigned to the treatment group had strains of influenza A/England/333/80 (H1N1) isolated. Two left the study for reasons unrelated to the treatment. Seventeen of 21 patients admitted as controls had the same virus isolated and constituted the control group. Fifteen of seventeen control patients received saline inhalations corresponding to period of ribavirin aerosol treatment. The patients' mean age was 21 years; 5 of 14 treated were males and 7 of 17 controls were females. One patient had received influenza vaccine more than 24 months before admission; none of the others recalled receiving vaccine. Seven of 14 treated and 5 of 17 controls thought they had influenza within the past two years.

Evaluation of Illness and Fever

The degree of illness was assessed at admission and each morning thereafter until recovery. The physician completed a questionnaire at each examination that focused primarily on the severity of respiratory and systemic illness. The questions specifically covered abnormalities of eyes, ears, throat, chest and lungs, systemic illness as measured by the degree of malaise or prostration, feverishness or chilliness, headache, muscle or joint aches, anorexia or nausea, as well as other findings. After these were recorded in the chart, the physician recorded his opinion, 0 to 3+, of the degree of rhinitis, pharyngitis, tracheobronchitis, systemic illness or other kinds of involvement. Pneumonia was not seen. The major abnormalities at time of admission were pronounced prostration, headache, eye aches and photophobia, lumber muscle and joint aching—findings used to measure systemic illness. Temperatures were recorded every four hours.

Clinical Laboratory Studies

The following hematologic studies were performed at admission and at discharge from the hospital: hematocrit, red cell count, white cell count, differential white cell count, hemoglobin concentration and reticulocyte count. Biochemical tests as follows were performed on admission, at discharge, and one month later: indirect bilirubin, direct bilirubin, total bilirubin, blood urea nitrogen, creatinine, glucose, calcium, phosphorus, albumin, total protein, alkaline phosphatase, serum aspartate transminase (ASP), and serum alanine transaminase (ALT), lactic dehydrogenase (LDH), creatine phosphokinase (CPK), uric acid, and aldolase. Throat swabs for bacterial culture were obtained on admission; no bacterial species deemed to be the cause of illness were isolated. Electrocardiograms and chest roentgenograms were made on admission; none were abnormal.

Virus Isolation and Quantitation

On admission a throat swab was collected in veal infusion broth containing 100 μg/ml penicillin and 100 μg/ml of streptomycin from every patient who entered the study. It was refrigerated until inoculated into Madin-Darby canine kidney, rhesus monkey (LLC), human epithelial carcinoma (Hep-2), and human embryo fibroblast (WI-38) cell cultures. Standard diagnostic procedures including immunofluorescence were employed. Baxter, et al. Maintenance of viability and comparison of identification methods for influenza and other respiratory viruses of humans; J. Clin. Microb. 1977; 6(2):19–22. Dowdle, W. A., et al. Influenza viruses. In Lennette, E. H., Schmidt, N.J., eds. Diagnostic Procedures for Viral Rickettsial and Chlamydial Infections, Washington, D.C.: Amer. Public Health Assoc. Inc. 1979:585. Frank, A. L., et al. Comparison of different tissue cultures for isolation and quantitation of influenza and parainfluenza viruses 1979; J. Clin. Microbiol. 10:32–36. The strains from patients in the study were related to influenza A/Brazil/11/78(H1N1). Several of the isolates were further characterized in ferret antisera and in monoclonal antibody tests. All were found to resemble A/England/333/80(H1N1) (personal communication, H. R. Six).

The titer of influenza virus was determined on nasal wash specimens taken at admission and twice daily thereafter for about three days. With the head tilted back and the breath held, a few mls. of sterile lactated Ringer's solution was instilled into each nostril. The head was then bent forward and the liquid blown into a paper cup. This was repeated until about 8 ml. of fluid was collected. The sample was then frozen at 70° C. until titration was carried out.

Virus titration was performed in 6×4 (1.5 cm. dia.) multiwell plastic dishes (Falcon Plastics No. 3008, Oxnard, Calif.) with MDCK cells. One-tenth ml. of undiluted and serial 10-fold dilutions of nasal wash fluid were inoculated onto the surface of each of four wells of freshly washed tissue culture. After one hour the inoculum was removed by aspiration and one ml. of Eagle's minimum essential medium containing 2 μg/ml of trypsin (Worthington) and antibiotics were added. End points were determined after 48 hours' incubation by hemadsorption with 0.075 percent guinea pig red cells.

Tests of Nasal Wash Specimens for Ribavirin

Pre-and post-treatment nasal wash specimens (lactated Ringer's solution) were heated to 65° C. for one-half hour to destroy virus. Then, to a measured volume of each specimen 0.1 ml. of one 1:1000 dilution of an egg pool of influenza A/England/333/80 (H1N1) virus from a patient was added. The titer of virus was determined in one pre-treatment and four post-treatment specimens from each of six patients as described above.

As a drug control, ribavirin (50 μg/ml, 100 μg/ml, and 500 μg/ml) was added to a nasal wash specimen from a volunteer. One specimen of each ribavirin concentration was heated at 65° C. for one-half hour to measure the effect of heat on ribavirin; another was kept at room temperature. Virus was added and titration carred out as above. Heated and unheated material gave nearly identical results. Results of 50 μg/ml tests were nearly identical with pre-treatment control specimens.

Hemagglutination-inhibition-antibody Titration

Acute and convalescent speciments were titrated in plastic dishes, 8×12, 0.25 ml. conical wells (Linbro-Titerek, Hamden, cn 06517), by a standard method. Dowdle, W. A., et al. Influenza viruses. In Lennette, E. H., Schmidt, N. J., eds. Diagnostic Procedures for Viral Rickettsial and Chlamydial Infections, Washington, D.C.: Amer. Public Health Assoc., Inc. 1979:585. Two antigens, influenza A/Brazil/11/78 (H1N1) and influenza A/Bangkok/1/79 (H3N2), were used in the tests.

Ribavirin Small-particle Aerosol Treatment

Treatment was begun within one hour of admission to the hospital. Ribavirin dissolved in sterile distilled water in amounts necessary to provide the specified aerosol concentration was added to the reservoir 38 of the aerosol generator.

Table 2 shows the hours of treatment and estimated retained dose of ribavirin. Ribavirin dosage was calculated from one minute expiratory volumes determined daily using the Bourn ventilation monitor LS75 (Bourn Company, Riverside, Calif. 92503) with nose clips. Concentrations of ribavirin in aerosol were determined spectrophotometrically at 207 nm wave lengths from samples obtained in all glass impingers. Knight, V., et al. Lack of interference of guanosine with ribavirin aerosol treatment of influenza A infection in mice. Vol. 20 (No. 4), pp. (not available) Antimicrob. Ag. Chemother. 1981.

0 was the period from admission about midday to midnight, essentially pretreatment temperatures. These were nearly equal in treated and control groups. The following day (day 1) temperatures in both groups had declined but again were nearly equal. By day 2, however, treated patients had a mean elevation of 36.9° C. compared to 37.4° C. for controls, a difference that was highly significant. The trend continued although almost all of the treated patients had recovered and had been discharged by day 3.

TABLE 3

| Mean Maximum Daily Temperatures in Treated and Control Patients | | | |
|---|---|---|---|
| | Calendar Day | | |
| | 0 | 1 | 2 |
| TREATED | | | |
| Temperature | 39.4° C. | 38.6° C. | 36.9° C. |
| N | 14 | 14 | 13 |
| CONTROL | | | |
| Temperature | 39.2° C. | 38.6° C. | 37.4° C. |
| N | 17 | 17 | 16 |
| One-tailed t-statistic | NS | NS | .003 |

The duration of fever was studied by measuring the hours to sustained reduction of temperatures below 37.4° C. This value was arbitrarily chosen, but the results were similar if values of 37.2° or 37.8° C. were used as a basis of comparison. In the comparison (Table 3), treated patients had fever as described above for a mean of 22.8 hours versus 38.1 hours for controls, a highly significant shortening of the period of fever. The mean period of illness before admission (treatment was begun within one hour of admission) was almost identical in the two groups; both were observed after defervescence for mean periods of about 18 hours.

Systemic Illness in Treated and Control Patients

TABLE 4

| Hours from Onset to Admission and Admission to Sustained Afebrile State (37.4° C.) in Treated and Control Patients | | |
|---|---|---|
| | Onset to Admission | Admission to Afebrile |
| TREATED (N = 14) Mean hours | 13.7 | 22.8 |
| CONTROL (N = 17) Mean hours | 13.6 | 38.1 |
| One-tailed t-statistic | NS | .00 |

TABLE 2

| | Estimated Retention of Ribavirin Aerosol by 14 Patients According to Calender Day | | | | | | | |
|---|---|---|---|---|---|---|---|---|
| | DAY 0 | | DAY 1 | | DAY 2 | | | |
| | Hours of Treatment | Estimated Retained Dose, Mg | Hours of Treatment | Estimated Retained Dose, Mg | Hours of Treatment | Estimated Retained Dose, Mg | Hours | Dose |
| Range | 5.5–10 | 270–602 | 6–12.5 | 262–867 | 1–13.5 | 52–728 | 15–35.5 | 664–1962 |
| Mean | 7.7 | 399 | 11.6 | 578 | 4.4 | 217 | 22.7 | 1147 |
| Mean retention mg/hr | 52 | | 50 | | 49.3 | | 51 | |

Dose determination: concentration ribavirin in aerosol (ug/l) × minute volume (liters) × 0.7 (retained fraction, based on tests performed in this laboratory) × number of minutes treated divided by 1000 = retained dose on mg.

RESULTS

Febrile Response in Treated and Control Patients

The mean maximum temperatures in treated and control patients by calendar days are shown in Table 3. Day The systemic illness scores in treated and control patients are shown in Table 5. At admission both groups of patients had nearly equal degrees of severe systemic illness. However, by the next morning, a period of less than 24 hours, treated patients had improved greatly (P=0.004). The trend continued the next day, but control patients had also shown great improvement by this time as well. Local findings of rhinitis, pharyngitis and tracheobronchitis were never severe and showed only a trend of less illness in treated patients on day 2 (less than 48 hours after admission).

Illness Score in Treated and Control Patients

TABLE 5

|  | Calendar Day | | |
| --- | --- | --- | --- |
|  | 0 | 1 | 2 |
| TREATED | | | |
| Systemic Illness, mean score | 2.64 | 1.50 | 1.0 |
| Rhinitis, pharyngitis, tracheo-bronchitis, mean score | 1.52 | 1.31 | 0.77 |
| N | 14 | 14 | 12 |
| CONTROL | | | |
| Systemic illness, mean score | 2.56 | 2.18 | 1.38 |
| Rhinitis, pharyngitis, tracheo-bronchitis, mean score | 1.49 | 1.31 | 1.14 |
| N | 17 | 17 | 16 |
|  | P-values* | | |
| Systemic illness | NS | .004 | .07 |
| Rhinitis, pharyngitis, tracoeo-bronchitis | NS | .NS | .07 |

*Wilcoxon rank sum test, one tailed.

Virus Shedding in Treated and Control Patients

Virus shedding was measured at admission and twice daily thereafter. There was a rapid reduction in mean virus titer in treated patients that is highly significant at 18 hours after admission. There was a slight secondary rise in virus titer in both treated and control groups due to lack of cultures from some recovered patients.

Failure to Demonstrate Ribavirin in Nasal Wash Specimens

Since ribavirin was administered by inhalation, it was possible that specimens for virus quantitation obtained after treatment would be affected by drug contaminating the nasal wash fluid. The results of a study of this question show almost identical virus growth in pretreatment and post-treatment specimens at all dilutions indicating that no significant amount of ribavirin was present in nasal wash specimens obtained for virus titration.

In a further study the nasal wash material was obtained from a normal volunteer and 0.1 ml aliquots containing 50 µg/ml, 100 µg/ml and 500 µg/ml were tested as above. Some inhibition of virus growth was observed in undiluted specimens containing 100 µg/ml and 500 µg/ml. At 1:10 dilution only specimens containing 500 µg/ml inhibited virus growth. At higher dilutions no drug effect was detected. A concentration of 50 µg/ml showed no inhibitory activity. Thus concentrations of ribavirin of up to 50 µg/ml would not have been detectable in these tests.

Serologic Response to Infection

Acute and convalescent hemagglutination inhibition antibody titers were made. The titers to the H1N1 virus were low in both treated and control groups at admission. There was a trend of greater serologic response in treated patients (P=0.084). There was no rise in titers to the H3N2 virus in convalescence from a 1:14 mean acute titer.

Clinical Chemical Tests in Treated and Control Patients

Clinical chemical tests were performed on 14 treated and 17 control patients at admission; at discharge there were 13 treated and 15 controls, and at one month there were 11 and 17 sets of tests performed.

Drug toxicity would be expected to be manifested in specimens taken at discharge from the hospital shortly after stopping treatment. In the whole series of tests the only significant difference between means of treated and control patients at this time was an abnormal elevation of creatine phosphokinase tests in treated patients (mean values: treated 284 units/ml, control 81 units/ml) (P=0.04, t-test). This result was due to high values in 5 treated patients, but all 5 were abnormally elevated before treatment. At followup 4 treated and 4 control patients had abnormally high CPK values.

The direct bilirubin test was significantly elevated at admission in treated patients compared to controls (mean: treated 0.24 mg/dl, controls 0.12 mg/dl) (P=0.03, t-test) due largely to a value 1.0 mg/dl in one patient. This elevation reduced to 0.5 mg/dl at discharge and was normal at one month. Glucose and total protein levels were both significantly higher in control patients at discharge, but were not considered to be clinically significant. There were sporadic, slight elevations over normal values in a few other tests at all three time periods in treated and control patients that were not considered to indicate drug toxicity.

Hematologic Findings

There were no significant changes in hematocrit, hemoglobin, and red cell count between treated and control groups at admission or discharge.

The total white blood cell count was low at admission (about 6,000, typical of influenza) and still lower at discharge (about 4500) in both treated and control groups, which is consistent with evolving influenza illness in patients who are admitted early in their disease. Consistent with the drop in white count was a major reduction in absolute polymorphonuclear count. The absolute lymphocyte count, however, more than doubled by the time of discharge, again consistent with evolving influenza illness. Note also the lowering of reticulocyte counts in both treated and control patients at discharge. (P=0.01).

Clinical Tolerance of Ribavirin

One patient in whom influenza was not diagnosed experienced nausea and vomited several times during 2½ days of treatment. It was considered probable that he had enteroviral infection that was responsible for his gastrointestinal disease.

This example demonstrates the effectiveness and safety of ribavirin-particle aerosol in the treatment of influenza A/England/333/80 (H1N1) infection in a group of college students.

EXAMPLE 2

In this example, the effectiveness of ribavirin small particle aerosol treatment of influenza pneumonia caused by a strain of influenza A/Bangkok/79(H3N2) is shown. The patient, a 61 year old man, entered the hospital dyspneic with fever, profound anoxemia, and in semi-coma. Family members had influenza in previous days. Chest X-ray showed diffuse bilateral infiltrates consistent with influenzal pneumonia and pulmonary edema. Electocardiogram revealed acute myocardial infarction presumed to have been precipitated by influenza. Influenzal pulmonary infection was proved by the presence of high titers of influenza virus in his tracheal aspirate and, based on clinical findings, the diagnosis was probably influenzal pneumonia.

The patient was treated with ribavirin aerosol for 60.5 hours during the course of five days in intensive care. The ribavirin aerosol generator was operated with a mixture of 60% oxygen and 40% air by means of an oxygen mixer. The aerosol flowed at a rate of 10 liters per minute.

Ribavirin aerosol was fed into the tubing attached to the patient's tracheal catheter during the patient's exhalation. This tubing had a volume of 650 cc. When assisted inspiration occurred using a monoghan 225 respirator, 650 cc of aerosol was pushed into the patient's respiratory tract by a 700 cc volume of 60% oxygen from the respirator. The patient thus received 6500 cc of aerosol per minute. With an estimated retention factor of 60% and an aerosol concentration of ribavirin of 180 mcg/l, the patient retained 42 mg of ribavirin per hour or about 2.5 grams in 60.5 hours. Improvement was steady and without complications; he was discharged on the fourteenth hospital day. At follow-up one month later he was well, having recovered from both myocardial infarction and influenzal pneumonia.

This example demonstrates the effectiveness and safeness of the treatment of a patient with severe influenza pneumonia (influenza A/Bangkok/79(H3N2)) and acute myocardial infarction in which the patient recovered promptly with ribavirin small particle aerosol treatment. It is believed that the treatment was an important factor in his recovery.

While there are inconsistencies, it appears that under some circumstances ribavirin has therapeutic activity by the oral route in treatment of influenza. The present clinical trials establish the effectiveness of ribavirin treatment of influenza by the mechanism of the deposition of the drug directly on the surface of the lungs and other portions of the respiratory tract. The data show that the treatment is safe.

EXAMPLE 3

Amantadine small-particle aerosol treatment as described in Example 1 was used in three patients with influenza A infection with good tolerance and apparent therapeutic effect. The drug is not effective in influenze B infection. When amantadine was given by the oral route, it had little effect on virus shedding and has not been very effective in cases with pulmonary complications.

EXAMPLE 4

In this example, the alternate arrangement of FIG. 3 was employed in a randomized, controlled study, in which ribavirin small-particle aerosol was found to be effective in the treatment of influenza B virus infection in a group of college students. Eleven treated patients experienced significantly more rapid defervescence, disappearance of systemic illness, and reduction of virus shedding in nasal secretions than ten control patients treated with a saline aerosol. Antibody response to infection was similar in both groups. The treatment was well tolerated, and hematologic and clinical chemical tests demonstrated no toxicity. The estimated dose of ribavirin aerosol retained was about 2 g in 39 hours of treatment during the first 60 hours in the hospital. A specific description of this study is reported in JAMA, May 20, 1983, Vol. 249, No. 19.

EXAMPLE 5

The present invention is effective for the treatment of asthma, lung cancer, and the like, that is, diseases in which direct deposition of the therapeutic agent on the interior surfaces of the lung, nose and throat may respond to administration of the drug in small particle aerosol in sufficient dose. Small particles (1 to 2 microns mass median diameter) are about 70% retained after inhalation and distribute in almost equal concentrations over the lining membranes of the nose, throat, trachea, bronchi, and the peripheral areas of the lung. Deposition occurs within seconds of initiation of treatment and thus can exhibit immediate therapeutic effect. Drugs given by other routes must be transported to the lung by the blood stream, which may take considerable time. There are many potential applications of small particle aerosol treatment of various diseases of the lung and respiratory tract such as medications for asthma, cancer and microbial or parasitic infection; for example, Isoproterenol, Phenylephrine, Metaproterenol small particle aerosol treatment of asthma; Bactrim, Pentamidine small particle aerosol treatment of pulmonary parasitic infection (Pneumocystis Carinii); and Cyclophosphamide, Methotrexate, Fluorouracil, 3-Deazaguanine treatment of cancer.

The present invention therefore is well suited and adapted to attain the objects and has the advantages mentioned as well as others inherent therein.

While presently preferred embodiments of the invention have been given for the purpose of disclosure, other uses and changes can be made therein which are within the spirit of the invention as defined by the appended claims.

What is claimed is:
1. A nebulizer comprising,
   a nebulizer chamber,
   a nebulizer head in the nebulizer chamber having at least one atomizer port,
   a drug line in fluid communication between the port and a source of drug,
   a face mask,
   an outflow line extending from the nebulizer chamber to the face mask for providing aerosol containing drug to the patient,
   means for providing air to the nebulizer head,
   a combination exhaust and aerosol reservoir line adjacent the face mask in fluid communication with the outflow line and the face mask, said exhaust and aerosol reservoir line having an unobstructed passage,
   the combination exhaust and aerosol reservoir line effective to permit air exhaled by the patient and the aerosol containing drug to flow into the exhaust and aerosol line thereby flushing the exhaust and aerosol line of air exhaled when the patient is exhaling, and the aerosol containing drug to flow from the exhaust and aerosol line to the patient while inhaling.
2. A nebulizer comprising,
   a nebulizer chamber,
   a drug chamber,
   a nebulizer head in the nebulizer chamber having at least one atomizer port,
   a drug line in fluid communication between the atomizer port and drug in the drug chamber, a face mask, an outflow line extending from the nebulizer chamber to the face mask for providing aerosol containing drug to a patient, means for providing air to the nebulizer head, a combination exhaust and aerosol reservoir line adjacent the face mask in fluid communication with the outflow line and the face mask, said exhaust and aerosol reservoir line having an unobstructed flow passage, and the combination exhaust and aerosol reservoir line effective to permit air exhaled by the patient and the aerosol containing drug to flow into the exhaust and aerosol reservoir line thereby flushing the exhaust and aerosol reservoir line of air exhaled when the patient is exhaling, and the aerosol containing drug to flow from the exhaust and aerosol line to the patient while inhaling, a dryer connected in the outflow line effective to dry the aerosol containing drug and thereby shrink its particle size, the outflow line's flow passage between the dryer and the face mask being unobstructed.

3. A nebulizer comprising, a nebulizer chamber, a drug chamber, a nebulizer head in the nebulizer chamber having at least one atomizer port, a drug line in fluid communication between the atomizer port and drug in the drug chamber, an outflow line having a discharge end extending from the nebulizer chamber for providing aerosol containing drug to the patient, means for providing air to the nebulizer head, a combination exhaust and aerosol reservoir line adjacent the outflow line's discharge end and in fluid communication with the outflow line and its discharge end, the exhaust and aerosol reservoir line having an unobstructed flow passage, the combination exhaust and aerosol reservoir line effective to permit air exhaled by the patient and the aerosol containing drug to flow into the exhaust and aerosol line thereby flushing the exhaust and aerosol line of air exhaled when the patient is exhaling and the aerosol containing drug to flow from the exhaust and aerosol line to the patient while inhaling, a dryer connected in the outflow line effective to dry the aerosol containing drug and thereby shrink its particle size, the outflow line downstream of the dryer to the patient being unobstructed, and an air dilution line connected to the dryer in fluid communication with the outflow line.

4. The nebulizer of claims 2 or 3 where, the drug chamber and the nebulizer chamber are one and the same chamber.

5. The nebulizer of claims 2 or 3 where, the nebulizer head has a plurality of atomizer ports, the drug line extends from the drug chamber to one of the atomizer ports effective to provide drug to the nebulizer head to be aerosolized, and includes a line extending from each of the other atomizer ports to fluid not aerosolized in the nebulizer chamber, and a return line extending from the fluid in the nebulizer chamber to the drug chamber effective to return excess of the fluid to the drug chamber.

6. The nebulizer of claims 2 or 3 where, the nebulizer head has a plurality of atomizer ports, the drug supply line extends from the drug chamber to one of the atomizer ports effective to provide drug to the nebulizer head to be aerosolized, and includes a line extending from each of the other atomizer ports to fluid not aerosolized in the nebulizer chamber, a return line extending from the fluid in the nebulizer chamber to the drug chamber effective to return excess of the fluid to the drug chamber, and the return line has a vertically-extending opening partially extending into the fluid in the nebulizer chamber effective to permit air to return to the drug chamber in the return line is small bubbles.

7. The nebulizer of claims 2 or 3 where, the nebulizer chamber and the drug chamber are separate chambers, the nebulizer head has a plurality of atomizer ports, the drug line comprises separate lines extending from the drug chamber to one each of the atomizer ports, and includes a return line extending from the nebulizer chamber to the drug chamber effective to return unaerosolized drug to the drug chamber.

* * * * *